Dec. 16, 1975 M. C. VAN STAAVEREN Plant Pat. 3,816
CARNATION PLANT "BELLITA"
Filed Oct. 15, 1974
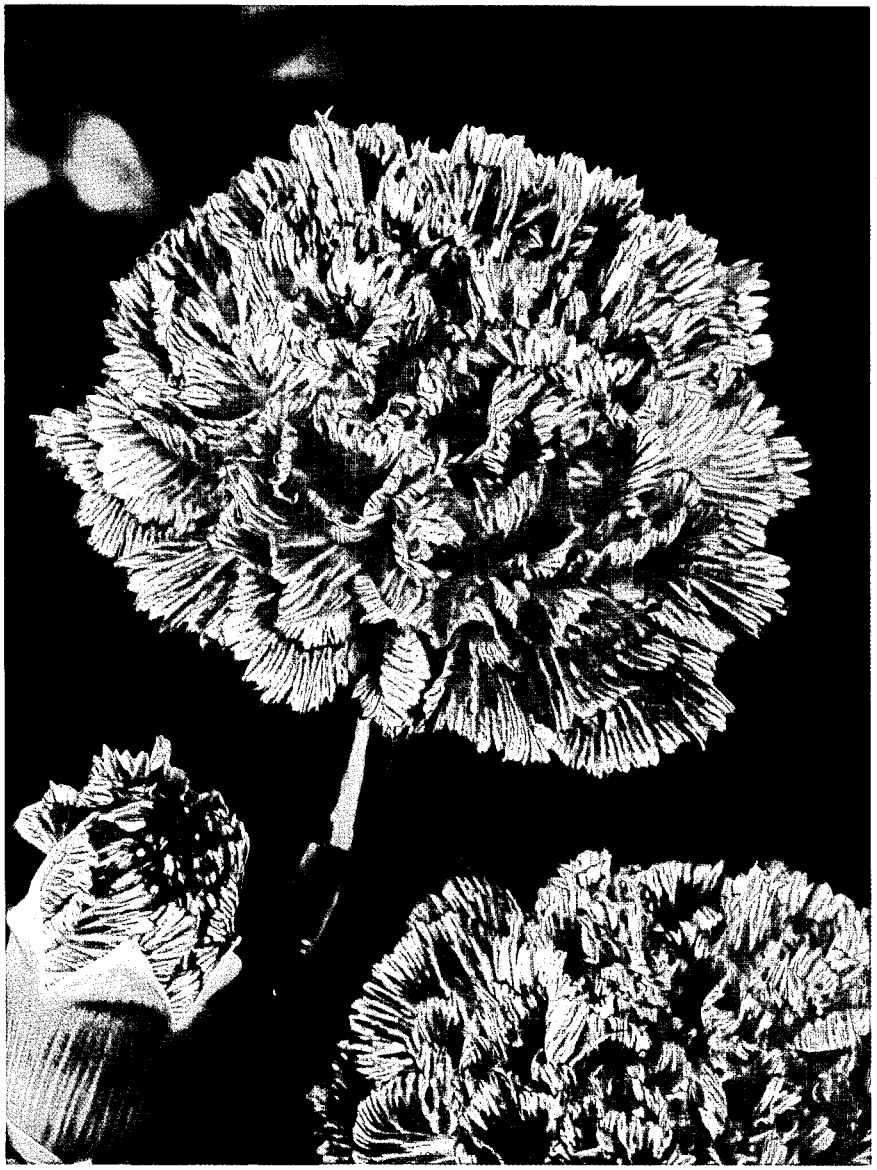

United States Patent

Plant Pat. 3,816

Patented Dec. 16, 1975

3,816

CARNATION PLANT "BELLITA"

Maurits C. van Staaveren, 30 Hornweg,
Aalsmeer, Netherlands

Filed Oct. 15, 1974, Ser. No. 514,427

Int. Cl. A01h 5/00

U.S. Cl. Plt.—70 1 Claim

ABSTRACT OF THE DISCLOSURE

A new variety of carnation plant of the Sim, or American, type intended to be grown for the production of cut flowers, the new plant being distinguished by the unique color pattern of the flower petals which have a strong red color over a yellow background to present a bright flamy appearance for the full bloom, the plant having a continuous blooming habit with flowers of medium size carried on long, strong stems.

BACKGROUND OF THE INVENTION

This new carnation plant was discovered by me in 1972 as a sport of the variety Bella (unpatented) grown by me at Aalsmeer, Netherlands. The very attractive coloring of this sport caused me to propagate it by means of cuttings to observe its growth characteristics and flower production and the satisfactory results have led to further propagation at Aalsmeer, Netherlands, through many generations, by means of cuttings, all of which have demonstrated that the novel and distinctive characteristics of this new variety of carnation plant hold true from generation to generation and are firmly fixed.

DESCRIPTION OF THE DRAWING

This new variety of carnation plant is illustrated by the accompanying photographic drawings which shows, in full color, the colors shown being as nearly true as it is reasonably possible to obtain by conventional photographic procedures.

DESCRIPTION OF THE NEW PLANT

The following is a detailed description of my new variety of carnation plant with color designations according to the R.H.S. Colour Chart of The Royal Horticultural Society, published at London, England, in collaboration with The British Colour Council.

THE PLANT

Origin: Sport.
Parentage: Bella (unpatented).
Classification:
*Botanic.*—*Dianthuscaryophyllus.*
*Commercial.*—Carnation.
Form: Bush.
Height: About 2 meters.
Growth: Vigorous and erect with strong flexible stems which are slightly ribbed and a little flattened, the longest internode (the fourth) being about 118 mm. long. The stems are dark green in color with a blue-grey waxy layer.
Branching: Upright with each branch having long flowering stems which bear a single blossom.
Foliage: Quantity—Medium, about 12 leaves to each branch. In winter 16–21 leaves to each branch.
*Size of leaf.*—About 14 cm. long and about 15 mm. wide.
*Shape of leaf.*—Long lanceolate with acute tip; amplexicaul with a slight longitudinal central groove at the tip end and being generally flat for major part of leaf length.
*Texture.*—Smooth.
*Color.*—Dark green with a blue-grey waxy layer.

THE BUD

Size: About 35 mm. long and 30 mm. in diameter.
Shape: Dome-shaped.
Color: Yellow-green.
Sepals: Hooded over bud until opening, tips curl back under flower when bloom opens.
*Shape.*—Spade-shape with mucronate tip.
*Color.* — Inside—Grey/green. Outside — Yellow/green with white tip ends.
*Number.*—Five.
Calyx: Size—Large, about 35 mm. high.
*Shape.*—Bell-shaped.
*Aspect.*—Smooth.
*Splitting.*—Occasionally, depending upon weather.
Opening: Medium opening rate, depending on the weather conditions.
Peduncle: Length—60 to 70 cm.
*Strength.*—Erect and strong.
*Aspect.*—Smooth.
*Color.*—Dark green with blue/grey waxy layer.

THE FLOWER

Blooming habit: Continuous and profuse. Has a tendency to give fewer blooms in winter.
Size: Medium, like Sim-type flowers.
*Diameter.*—90 mm.
*Depth.*—30 mm.
Borne: Singly.
Shape: Bell-shaped. Top view—Rounded. Side view—Anguar, outer petals tend to spread toward downwardly hanging position.
Petalage: Number of petals—About 70.
*Form of petals.*—Claw—About 25 mm. long, 2 mm. wide at the base and widening to 7 mm. at the blade. Blade—Fan shaped, with asymmetric base, about 28 mm. high and about 32 mm. wide. Blade is median folded and has a crenated-dentated edge with indentations of ¼ to ½ mm.
*Color.*—Top side — Background — Yellow 19C–D with radial red striped flamy overlay of Red 43B–C. Midway of the blade the pattern blends with a darker shade 43B which runs almost to the base. Under side—The background is Yellow 19C–D and the overlay pattern is somewhat brighter 43–C.
*Texture.*—Woody.
*Appearance.*—Somewhat greyed.
Peduncle: Sturdy, upright. 60 to 70 cm. long. Color: Dark green with blue/grey waxy overlay.
Persistance: Petals dry, bloom stays upright.
Fragrance: Slight fragrance.
Lasting quality: On plant — About 14 days. As cut flower—About 8 to 10 days.

REPRODUCTIVE ORGANS

Stamens: Small in number, predominantly petaloid.
*Filaments.*—1 to 2 cm. in length. Color: White.
*Pollen.*—Yellow in color.
Pistils: Number—one.
*Style.*—1½ to 2 cm. long.
*Stigma.*—Color—Yellow/orange.
Ovary: Spindle-shaped.

This new variety of carnation plant most nearly resembles its parent Bella but is distinguished from it by the stronger color pattern of flower petals and the darker color of the background over which the red pattern appears, thus giving the flower a very favorable aspect for cut flower usage.

I claim:

1. The new and distinct variety of carnation plant, substantially as herein shown and described, characterized by the strong color pattern of its flowers, the long strong stems on which the flowers are borne, and its vigorous and very tall growth habit.

No references cited.

ROBERT E. BAGWILL, Primary Examiner